US007828839B2

United States Patent
Cook et al.

(10) Patent No.: US 7,828,839 B2
(45) Date of Patent: Nov. 9, 2010

(54) FLEXIBLE BARB FOR ANCHORING A PROSTHESIS

(75) Inventors: William A. Cook, Bloomington, IN (US); Michael P. DeBruyne, Bloomington, IN (US); Mark R. Frye, Bloomington, IN (US); Benjamin Nickless, Bloomington, IN (US); Thomas A. Osborne, Bloomington, IN (US); Ronan T. Young, Spencer, IN (US)

(73) Assignee: Cook Incorporated, Bloomington, IN (US)

( * ) Notice: Subject to any disclaimer, the term of this patent is extended or adjusted under 35 U.S.C. 154(b) by 400 days.

(21) Appl. No.: 11/849,858

(22) Filed: Sep. 4, 2007

(65) Prior Publication Data

US 2008/0033534 A1 Feb. 7, 2008

Related U.S. Application Data

(63) Continuation-in-part of application No. 10/642,513, filed on Aug. 15, 2003, which is a continuation-in-part of application No. 10/431,809, filed on May 8, 2003, now Pat. No. 7,081,132.

(60) Provisional application No. 60/381,046, filed on May 16, 2002.

(51) Int. Cl.
*A61F 2/06* (2006.01)
(52) U.S. Cl. .................................... 623/1.36
(58) Field of Classification Search ........ 623/1.15–1.36

See application file for complete search history.

(56) References Cited

U.S. PATENT DOCUMENTS

| 4,218,783 | A | 8/1980 | Reul et al. |
| 4,580,568 | A | 4/1986 | Gianturco |
| 4,902,508 | A | 2/1990 | Badylak et al. |
| 4,994,077 | A | 2/1991 | Dobben |
| 5,035,706 | A | 7/1991 | Giantureo et al. |
| 5,108,420 | A | 4/1992 | Marks |
| 5,116,564 | A | 5/1992 | Jansen et al. |
| 5,123,919 | A | 6/1992 | Sauter et al. |
| 5,147,389 | A | 9/1992 | Lane |
| 5,171,259 | A | 12/1992 | Inoue |

(Continued)

FOREIGN PATENT DOCUMENTS

EP 0 221 570 B2 5/1987

(Continued)

OTHER PUBLICATIONS

Karino et al., "Flow Through a Venous Valve and its Implication for Thrombus Formation," 36 Thrombosis Research 245-57 (1984).

(Continued)

*Primary Examiner*—Suzette J Gherbi
(74) *Attorney, Agent, or Firm*—Brinks Hofer Gilson & Lione

(57) ABSTRACT

A system for anchoring an endoluminal prosthesis comprises a barb. The barb comprises a base, a retractable body extending distally from the base towards a distal anchor, and a hinge disposed between the base and the anchor and spaced apart from the base. The anchor pivots about the hinge between a retracted configuration and an extended configuration. Additional devices, systems, and methods are disclosed.

19 Claims, 10 Drawing Sheets

U.S. PATENT DOCUMENTS

| | | | |
|---|---|---|---|
| 5,334,217 A | 8/1994 | Das | |
| 5,335,341 A | 8/1994 | Chana | |
| 5,358,518 A | 10/1994 | Camilli | |
| 5,375,612 A | 12/1994 | Cottenceau et al. | |
| 5,387,235 A | 2/1995 | Chuter | |
| 5,451,235 A | 9/1995 | Lock et al. | |
| 5,480,424 A | 1/1996 | Cox | |
| 5,489,295 A | 2/1996 | Piplani et al. | |
| 5,500,014 A | 3/1996 | Quijano et al. | |
| 5,527,355 A | 6/1996 | Ahn | |
| 5,562,697 A | 10/1996 | Christiansen | |
| 5,607,465 A | 3/1997 | Camilli | |
| 5,630,829 A | 5/1997 | Lauterjung | |
| 5,632,771 A | 5/1997 | Boatman et al. | |
| 5,643,312 A | 7/1997 | Fischell et al. | |
| 5,643,317 A | 7/1997 | Pavcnik et al. | |
| 5,693,084 A | 12/1997 | Chuter | |
| 5,707,388 A | 1/1998 | Lauterjung | |
| 5,709,707 A | 1/1998 | Lock et al. | |
| 5,711,969 A | 1/1998 | Patel et al. | |
| 5,713,950 A | 2/1998 | Cox | |
| 5,720,776 A * | 2/1998 | Chuter et al. | 623/1.36 |
| 5,733,325 A | 3/1998 | Robinson et al. | |
| 5,733,337 A | 3/1998 | Carr, Jr. et al. | |
| 5,746,766 A | 5/1998 | Edoga | |
| 5,800,456 A | 9/1998 | Maeda et al. | |
| 5,800,526 A | 9/1998 | Anderson et al. | |
| 5,810,847 A | 9/1998 | Laufer et al. | |
| 5,824,061 A | 10/1998 | Quijano et al. | |
| 5,824,063 A | 10/1998 | Cox | |
| 5,840,081 A | 11/1998 | Andersen et al. | |
| 5,843,164 A | 12/1998 | Frantzen et al. | |
| 5,843,167 A | 12/1998 | Dwyer et al. | |
| 5,855,597 A | 1/1999 | Jayaraman | |
| 5,855,601 A | 1/1999 | Bessler et al. | |
| 5,861,003 A | 1/1999 | Latson et al. | |
| 5,863,164 A | 1/1999 | Leistner | |
| 5,879,382 A | 3/1999 | Boneau | |
| 5,885,619 A | 3/1999 | Patel et al. | |
| 5,897,589 A | 4/1999 | Cottenceau et al. | |
| 5,907,893 A | 6/1999 | Zadno-Azizi et al. | |
| 5,921,995 A | 7/1999 | Kleshinski | |
| 5,955,110 A | 9/1999 | Patel et al. | |
| 5,957,949 A | 9/1999 | Leonhardt et al. | |
| 5,961,546 A * | 10/1999 | Robinson et al. | 623/1.14 |
| 5,968,053 A * | 10/1999 | Revelas | 606/108 |
| 5,968,096 A | 10/1999 | Whitson et al. | |
| 6,004,347 A | 12/1999 | McNamara et al. | |
| 6,027,525 A | 2/2000 | Suh et al. | |
| 6,077,281 A | 6/2000 | Das | |
| 6,113,612 A | 9/2000 | Swanson et al. | |
| 6,126,686 A | 10/2000 | Badylak et al. | |
| 6,183,495 B1 | 2/2001 | Lenker et al. | |
| 6,200,336 B1 | 3/2001 | Pavcnik et al. | |
| 6,214,025 B1 | 4/2001 | Thistle et al. | |
| 6,221,102 B1 | 4/2001 | Baker et al. | |
| 6,231,581 B1 | 5/2001 | Shank et al. | |
| 6,245,102 B1 | 6/2001 | Jayaraman | |
| 6,280,467 B1 | 8/2001 | Leonhardt | |
| 6,287,334 B1 | 9/2001 | Moll et al. | |
| 6,299,637 B1 | 10/2001 | Shaolian et al. | |
| 6,322,587 B1 * | 11/2001 | Quiachon et al. | 623/1.23 |
| 6,327,772 B1 | 12/2001 | Zadno-Azizi et al. | |
| 6,355,056 B1 | 3/2002 | Pinheiro | |
| 6,355,061 B1 | 3/2002 | Quiachon et al. | |
| 6,379,392 B1 | 4/2002 | Walak | |
| 6,409,752 B1 | 6/2002 | Boatman et al. | |
| 6,458,153 B1 | 10/2002 | Bailey et al. | |
| 6,464,720 B2 | 10/2002 | Boatman et al. | |
| 6,506,190 B1 | 1/2003 | Walshe | |
| 6,517,574 B1 | 2/2003 | Chuter | |
| 6,565,597 B1 | 5/2003 | Fearnot et al. | |
| 6,676,698 B2 | 1/2004 | McGuckin, Jr. et al. | |
| 6,814,748 B1 * | 11/2004 | Baker et al. | 623/1.14 |
| 6,849,087 B1 | 2/2005 | Chuter et al. | |
| 6,860,901 B1 * | 3/2005 | Baker et al. | 623/1.36 |
| 7,081,132 B2 | 7/2006 | Cook et al. | |
| 7,147,661 B2 * | 12/2006 | Chobotov et al. | 623/1.16 |
| 7,572,289 B2 * | 8/2009 | Sisken et al. | 623/1.36 |
| 2002/0055772 A1 | 5/2002 | McGuckin, Jr. et al. | |
| 2002/0099441 A1 | 7/2002 | Dehdashtian | |
| 2003/0236570 A1 | 12/2003 | Cook et al. | |
| 2004/0117004 A1 | 6/2004 | Osborne et al. | |
| 2005/0240259 A1 | 10/2005 | Sisken et al. | |
| 2009/0300798 A1 * | 12/2009 | Kok-Jacon et al. | 800/284 |

FOREIGN PATENT DOCUMENTS

| | | |
|---|---|---|
| EP | 0 497 620 B1 | 1/1992 |
| EP | 0 480 667 B1 | 4/1992 |
| EP | 0 539 237 A1 | 4/1993 |
| EP | 0 667 133 B1 | 8/1995 |
| EP | 0 691 108 B1 | 1/1996 |
| EP | 0 712 614 A1 | 5/1996 |
| EP | 0 712 614 B1 | 5/1996 |
| EP | 0 808 614 B1 | 11/1997 |
| EP | 0 850 607 A1 | 7/1998 |
| EP | 0 856 300 A1 | 8/1998 |
| EP | 0 920 842 A1 | 6/1999 |
| WO | WO 93/13712 A1 | 7/1993 |
| WO | WO 95/29646 A1 | 11/1995 |
| WO | WO 98/22158 A2 | 5/1998 |
| WO | WO 98/53761 A1 | 12/1998 |
| WO | WO 99/15224 A1 | 4/1999 |
| WO | WO 99/62431 A1 | 12/1999 |
| WO | WO 00/35352 A1 | 6/2000 |
| WO | WO 01/19285 A1 | 3/2001 |
| WO | WO 01/56500 A2 | 8/2001 |
| WO | WO 01/56500 A3 | 8/2001 |
| WO | WO 01/76509 A1 | 10/2001 |
| WO | WO 02/41764 A2 | 5/2002 |
| WO | WO 02/41764 A3 | 5/2002 |

OTHER PUBLICATIONS

Gomez-Jorge et al., "Percutaneous Deployment of a Valved Bovine Jugular Vein in the Swine Venous System," JVIR 931-6 (2000).

Pavcnik et al., "Percutaneous bioprosthetic venous valve," 35 Journal of Vascular Surgery 598-602 (2002).

* cited by examiner

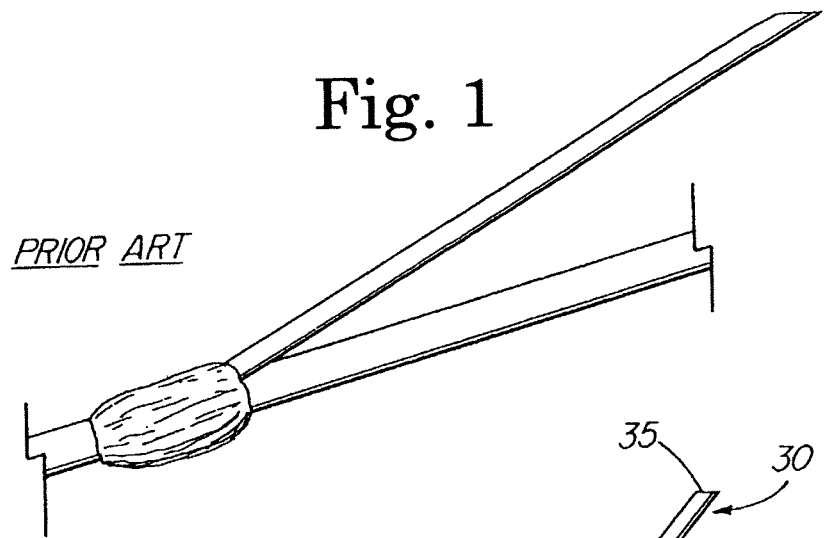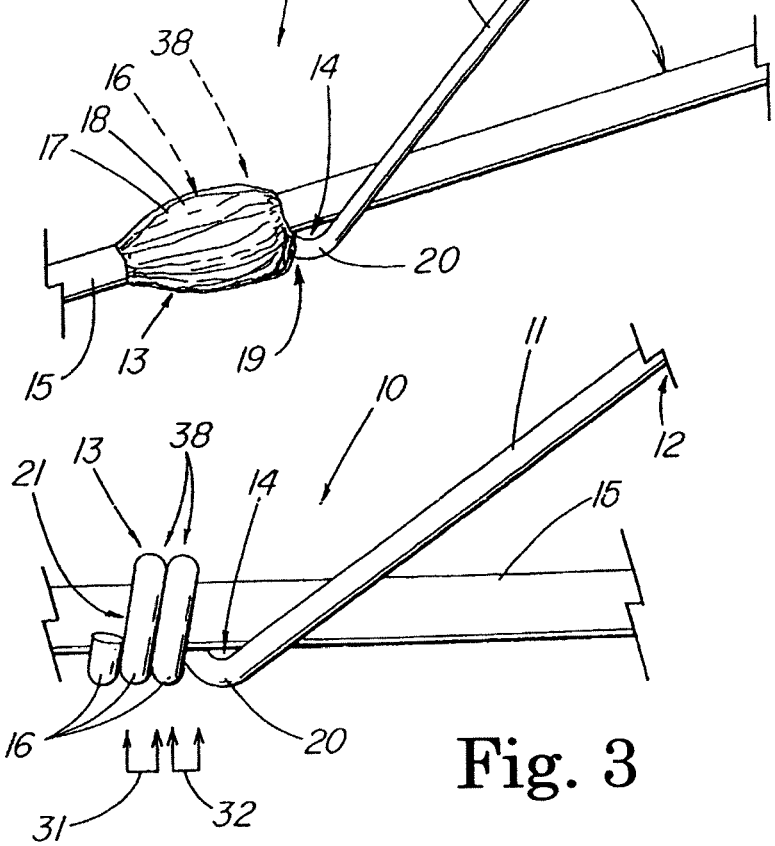

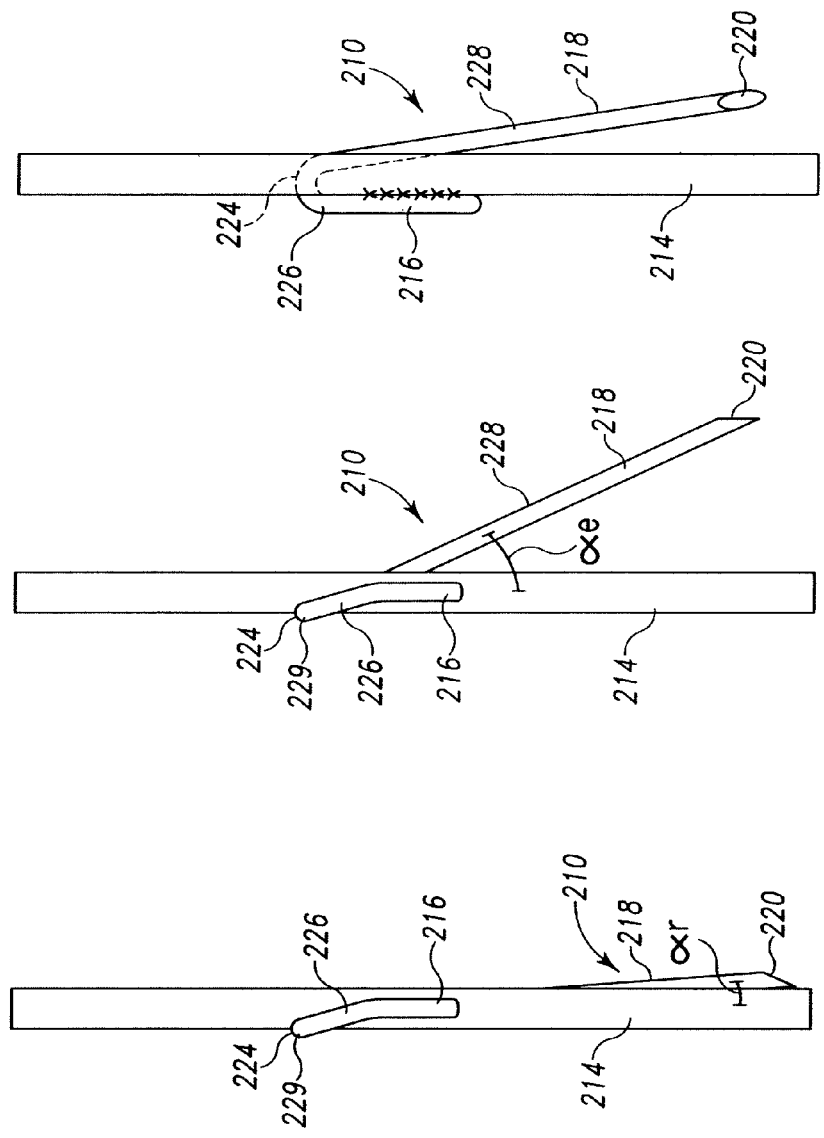

FLEXIBLE BARB FOR ANCHORING A PROSTHESIS

CROSS-REFERENCE TO RELATED APPLICATIONS

The present patent document is a continuation-in-part of application Ser. No. 10/642,513 filed Aug. 15, 2003, currently pending, which is a continuation-in-part of application Ser. No. 10/431,809 filed May 8, 2003, U.S. Pat. No. 7,081,132, which claims the benefit of the filing date under 35 U.S.C. §119(e) of U.S. Provisional Patent Application Ser. No. 60/381,046 filed May 16, 2002. All of the foregoing applications are hereby incorporated by reference.

BACKGROUND OF THE INVENTION

1. Field of the Invention

This invention relates to medical devices, more particularly to stents and other prosthetic devices having anchoring barbs.

2. Description of Related Art

The functional vessels of human and animal bodies such as blood vessels and ducts can occasionally weaken. For example, the aortic wall can weaken, resulting in an aneurysm. Upon further exposure to haemodynamic forces, such an aneurysm can rupture.

These medical conditions and similar pathologies can call for surgical intervention. The aneurismal aorta, for example, may be treated using an endoluminal prosthesis. Such an endoluminal prosthesis will exclude the aneurysm so that the aneurysm no longer grows, nor has the opportunity to rupture.

One endoluminal prosthesis which is useful for repair of aortic aneurysms is disclosed in PCT application WO 98/53761, which is incorporated herein by reference. This application discloses a prosthesis which includes a sleeve or tube of biocompatible prosthesis material such as DACRON® polyester fabric (trademark of E. I. DuPont de Nemours and Co.) or polytetrafluoroethylene (PTFE) defining a lumen. The WO 98/53761 prosthesis further includes several zigzag stents secured therealong. These stents can be, for example, Gianturco Z-stents, which are commercially available from Cook Inc., Bloomington, Ind.

The prosthesis of the PCT application WO 98/53761 is designed to span an aneurysm that extends along the aorta proximally from the two iliac arteries. This reference also discloses the manner of deploying the stent prosthesis in the patient utilizing an introducer assembly.

In the WO 98/53761 application, the material-covered portion of the single-lumen proximal end of the prosthesis bears against the wall of the aorta above the aneurysm to seal the aneurysm at a location that is spaced distally of the entrances to the renal arteries. Thin wire struts of a proximal fixation stent traverse the renal artery entrances without occluding them, since no prosthesis material is utilized along the proximal stent. The fixation stent secures the stent prosthesis in position within the aorta when the stent self-expands.

Blood vessels and other vessels can also become stenotic or occluded. For example, arteries can develop atherosclerotic plaques which can cause stenosis; eventually, a stenotic artery can become completely occluded. A stenotic or occluded artery can be treated by introducing self-expanding, balloon-expandable or shape-memory stents which expand the lumen at the site of stenosis or occlusion. Such a stent is disclosed in U.S. Pat. No. 6,464,720, which is incorporated herein by reference.

U.S. Pat. No. 6,464,720 discloses an expandable antistenotic stent made from a cannula or sheet of biocompatible material that includes at least one longitudinal segment comprised of a series of laterally interconnected closed cells. Each closed cell of a longitudinal segment is defined laterally by a pair of longitudinal struts that are interconnected at each end by a circumferentially adjustable member. When the stent is expanded using a balloon, the opposing circumferentially adjustable members deform to allow circumferential expansion of the longitudinal segment, while the length of the segment, as defined by the longitudinal struts, is maintained. Self-expanding versions of the stent utilize a nickel-titanium alloy. Other stents are disclosed in U.S. Pat. Nos. 5,632,771 and 6,409,752, which are incorporated herein by reference.

When endoluminal prostheses or antistenotic stents are implanted to treat these or similar conditions, it is important that they do not migrate under physiological forces. Pulsatile flow is a major force that stents encounter; thus stents and endoluminal prostheses tend to move downstream in the blood vessel in which they are placed.

If the stents or endoluminal prostheses do migrate, they can travel beyond the length of the vessel they are intended to treat. For example, if an antistenotic stent migrates, it will fail to keep the targeted portion of the vessel from restenosing. If an endoluminal prosthesis migrates, it can expose the aneurysm it was meant to treat. The aneurysm will then repressurize, presenting a risk of rupture.

Migration can be a significant problem in the placement of expandable stents and other endoluminal devices, especially when placed in the arterial region of the vascular system. Nowhere is the prevention of migration more important and more challenging than when placing a stent graft to repair an abdominal aortic aneurysm (AAA) where downstream migration of the device can result in the aneurysm no longer being excluded. If the aneurysm is no longer intact or subsequent rupture were to occur, the patient would then face an increased risk of death. Unlike surgically placed grafts which are sutured into place, only the radial forces of the stent would be available to hold the prosthesis into place.

If an endoluminal prosthesis migrates towards a branch vessel, it can partially or totally occlude it. Likewise, if a fenestrated endoluminal prosthesis migrates, it can occlude the branch vessel to which the fenestration was to permit blood flow. If this happens to a fenestrated thoracic endoluminal prosthesis, for example, important branch vessels (e.g. the common carotid) can be occluded, resulting in death. If this happens to an aortic abdominal endoluminal prosthesis with renal artery fenestrations, kidney function can be seriously impaired.

To address the problem of migration, stent graft manufacturers sometimes place a series of barbs or hooks that extend outward from the main body of the prosthesis, typically at its proximal end, either by attaching them to the stent frame with solder or by some other bonding technique, or to the graft material, typically by suturing. These barbs can be attached to the stent wire by wrapping, chemical bonding, welding, brazing, soldering or other techniques. For example, one embodiment of the prosthesis of the PCT application WO 98/53761 utilizes barbs which extend from the suprarenal fixation stents to engage the aorta wall, to thereby keep the graft from migrating.

However, barbs attached by these methods have been known to break off or bend because repeated physiological stresses, the cyclical loading caused by cardiovascular pulsatile forces in particular, cause mechanical fatigue and failure of the barb-stent junction. It has been observed that sutures attaching barbed stents to the graft material are subject to breakage due in part to the flexibility of the graft material and the considerable pulsatile forces of arterial blood acting on the device. These forces have been known to directly contribute to the detachment between the graft portion and anchoring stent. If the barbs were bent in the manufacturing process, the barbs are further weakened. Furthermore, the barbs are exposed to a physiological environment which is saline, oxygen-rich and acidic, and therefore tends to weaken the barb and its connection through corrosion.

It has also been further observed that barbs soldered or otherwise attached to the stent frame are subject to fracture, detachment, or other failure, especially when the forces become concentrated at a particular location along the stent graft. Unfortunately, simply making the barbs stronger to prevent fracture can result in increased damage to the anchoring tissue. Furthermore, adding rigidity to any outward-projecting barbs may compromise the ability of the device to be compressed and loaded into a delivery system. The use of multiple barbs can prevent catastrophic migration of the device, especially if there are a very limited number of barb failures. Yet, while a single barb failure should not result in the migration of the device and may not represent a problem clinically, barb fracture or failure is nevertheless currently classified as an adverse event that manufacturers seek to avoid.

One solution to address barb failure was disclosed in U.S. Pat. No. 5,720,776 to Chuter et al., depicted in FIG. 1, where the barb includes both a mechanical attachment, as well as the traditional solder bond. The mechanical attachment comprises a helical winding of a portion of the barb around a strut of the stent prior to addition of the solder joint to help protect the solder joint from failure. In addition, the barb is made laterally flexible to help accommodate forces acting at the anchor point. These improvements help ensure that the barb does not readily detach from the stent due to a failure of the solder joint alone. While the combination of both solder and a mechanical means to affix the barb to the stent has proved effective in most respects, this area of the barb remains most subject to stresses, such as from cyclic load resulting from the pulsatile action of the implant vessel.

Another issue with known barbs is that the radial force of a barb is pre-determined and is wholly a function of the barb design. Accordingly, there is generally no ability to effect or tune the radial force of a barb during the manufacture of the endoluminal prosthesis. A typical prior art barb, as shown in FIG. 1, includes an elongate body that extends generally linearly at an angle from the junction between the barb and the strut. The body is biased at an angle to the strut and the radial force at the tip of the barb is a function of the length of the arm, which is typically fixed. Because the barb cannot be tuned, a manufacturer must provide multiple barb designs to accommodate varying anchoring force demands.

SUMMARY

Various systems for anchoring an endoluminal prosthesis are disclosed throughout the specification and in the drawings. In one example, a system for anchoring an endoluminal prosthesis is provided and comprises a barb. The barb may comprise a base, a retractable body extending distally from the base towards a distal anchor, a hinge disposed between the base and the anchor and spaced apart from the base, a first arm disposed between the base and the hinge, and a second arm disposed between the anchor and the hinge. The anchor pivots about the hinge between a retracted configuration and an extended configuration.

When the barb is in the extended configuration, the first arm may be disposed at a generally acute angle with respect to the second arm. The angle between the first arm and the second arm may increase from the retracted configuration towards the extended configuration. The angle between the second arm and the base may increase from the retracted configuration towards the extended configuration. The first arm may extend distally in a first direction with respect to the base and the second arm may extend distally in a second direction with respect to the base that is generally opposite the first direction.

In some examples, a system may be provided and comprise a support structure and a barb. The support structure may comprise a strut and the barb base may be attached to the strut. The barb may have any of the features described above or throughout the specification.

At least a portion of the barb body may extend longitudinally along and circumferentially about the strut. The hinge may be spaced apart from the strut by a first distance in the extended configuration and by a second distance that is less than the first distance in the retracted configuration. The base of the barb may comprise a cradle having an inner contour corresponding with an outer contour of the strut. The anchor may be disposed radially outwardly from the support structure and the hinge may be disposed radially inwardly from the support structure. The first arm may have a length corresponding with a predetermined barb anchoring force.

Another system for anchoring an endoluminal prosthesis is described and comprises a support structure and a barb. The barb comprises a base, an anchor, and a hinge disposed between the base and the anchor and spaced apart from the base. The base may be attached to the support structure and the anchor may pivot about the hinge between a retracted configuration and an extended configuration.

The support structure may comprise a strut and the barb base may be attached to the strut. The hinge may be spaced apart from the strut by a first distance in the extended configuration and by a second distance that is less than the first distance in the retracted configuration. At least a portion of the barb distal of the base may extend longitudinally along and circumferentially about the strut. The barb may comprise an arm disposed between the base and the hinge, where the arm has a length corresponding with a predetermined barb anchoring force. The barb may further comprise a second arm disposed between the anchor and the hinge. The angle between the first arm and the second arm may increase from the retracted configuration towards the extended configuration.

Various methods are disclosed throughout the specification and in the drawings. For example, a method of tuning an anchor for an endoluminal prosthesis is disclosed and comprises the steps of providing a retractable barb and providing a support structure for an endoluminal prosthesis. The barb may comprise a proximal end and a distal end, where a distal portion of the barb comprises an anchor. The method may further comprise the steps of determining a free length of the barb that corresponds with a predetermined barb anchoring force, and selectively attaching the barb to the support structure so that the length of the barb that extends freely from the support structure is generally equal to the free length.

BRIEF DESCRIPTION OF THE DRAWINGS

FIG. 1 depicts a side view of a prior art barb soldered to the strut of a stent;

FIG. 2 depicts a side view of a stent barb having a stress-dispersing region;

FIG. 3 depicts a side view of the barb of FIG. 2 prior to attachment to the strut;

FIGS. 10A-10C depict side and front views of another exemplary retractable barb;

DETAILED DESCRIPTION OF THE PREFERRED EMBODIMENTS

Figure 4:
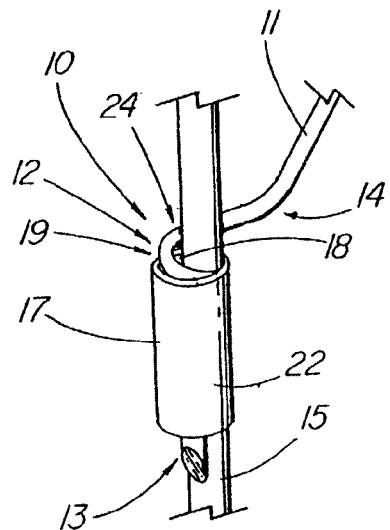
FIG. 4 depicts a side view of an embodiment of the present invention in which the barb is attached to the strut using a piece of cannula.

Throughout the specification, when referring to a barb or a portion thereof, the terms "distal" and "distally" shall denote a position, direction, or orientation along the barb that is generally towards or in the direction of the anchor, whereas the terms "proximal" and "proximally" shall denote a position, direction, or orientation along the barb that is generally away from or in the opposite direction of the anchor.

The term "generally acute" shall include angles that are less than or equal to 90°. The term "generally obtuse" shall include angles that are greater than or equal to 90°.

The term "prosthesis" means any device, object, or structure that supports, repairs, or replaces, or is configured to support, repair, or replace a body part or a function of that body part. It can also mean a device that enhances or adds functionality to a physiological system. Examples of prostheses include, but are not limited to, stents, grafts, stent grafts, venous or aortal valves, and vena cava filters. A prosthesis may be generally tubular and may comprise one or more lumens. Examples of tubular prostheses include straight, branched, and bifurcated prostheses.

The term "stent" means any device or structure that provides or is configured to provide rigidity, expansion force, or support to a body part, for example, a diseased, damaged, or otherwise compromised body lumen.

The term "expandable" means capable of being expanded. An expandable stent is a stent that is capable of being expanded, whether by virtue of its own resilience, upon the application of an external force, or by a combination of both. Expandable stents include both self-expanding and balloon-expandable devices. Self-expanding stents can be made of stainless steel, materials with elastic memory properties, such as NITINOL, or any other suitable material. An exemplary self-expanding stent includes Z-STENTS®, which are available from Cook Incorporated, Bloomington, Ind., USA. Balloon-expandable stents may be made, for example, of stainless steel (typically 316LSS, CoCr, etc.). Hybrid stents may be provided by combining one or more self-expanding stents or stent portions with one or more balloon-expandable stents or stent portions.

The term "strut," as used herein, may encompass a wire, bar, bend, or any portion of the prosthesis from which the barb may emanate, and is not necessarily limited to a strut as traditionally defined in the medical arts (typically, a thin section of the metal framework of a self-expanding or balloon-expandable stent).

The term "free length" refers to the length of the barb that extends freely from the attachment between the barb and the support structure to the distal end of the barb. For example, the free length of the barb may correspond with the length of a barb body that extends distally from a barb base.

FIGS. 2-8 depict a medical prosthesis 10, such as a stent, stent graft, valve, vessel occluder, filter, or other intraluminal medical device. A medical device may include one or more barbs 11, each comprising an anchor 12 that is sized and oriented to engage tissue for the purpose of anchoring the device and preventing the downstream migration thereof; a base 13 located about the physical union between the barb and the strut of the prosthesis 10 to which it is affixed; and a stress-dispersing region that forms a transition between the base 13 and anchor 12 of the barb 11. The stress-dispersing (or stress-reducing) region 14 comprises a section of the barb that has been shaped and configured to receive most of the forces acting upon the anchor 12 or moment arm of the barb as it bends and to distribute these forces throughout that region 14, rather than allowing them to be concentrated at a single point or relatively narrow region, such as the point of union 19 between the barb 11 and substrate of origin 15. The substrate of origin 15 may typically be a strut 15 of an intraluminal stent or other prosthesis to which the barb 11 is attached. For example, the barb may be sewn or otherwise attached directly to graft material or another portion of the prosthesis, or it may be formed integrally with the prosthesis. Additionally, the barb may be slidably affixed to the strut 15 to at least temporarily help relieve stresses about the point of union 19, which is generally defined as that point where the barb extends away from the substrate of origin 15 and/or the means of mechanical attachment 17 or bond 18 between the two.

It should be understood that the delineations between the anchor 12, the stress-dispersing portion 14, and the base 13, while primarily functional in nature, are not absolute. The base 13 may represent a well-defined and distinct section of the barb, or may merely represent the point of attachment or union with the strut 15 or framework of the prosthesis 10. In addition, the stress-dispersing region 14 may extend sufficiently away from the strut 15 that it also may penetrate adjacent tissue and serve to help anchor the stent. Generally, however, the stress-dispersing region 14 is located proximate to the point of union 19 such that the anchor 12 provides most of the anchoring function.

Although the addition of structure for reducing moment of stress can be placed anywhere along the length of the barb 11, it is most advantageous when located near the base thereof (point of union 19), especially if the stress load is being placed over a significant portion of the barb's length. For example, a series of bends or coils located exclusively at the midpoint of the barb 12 would provide little, if any, stress-relieving value if those bends become imbedded in tissue. In such a situation, the stress moment caused by the torsional and other bending forces acting on the barb would be transferred down toward the barb's base where stress-dispersing structure is lacking.

Figure 8:
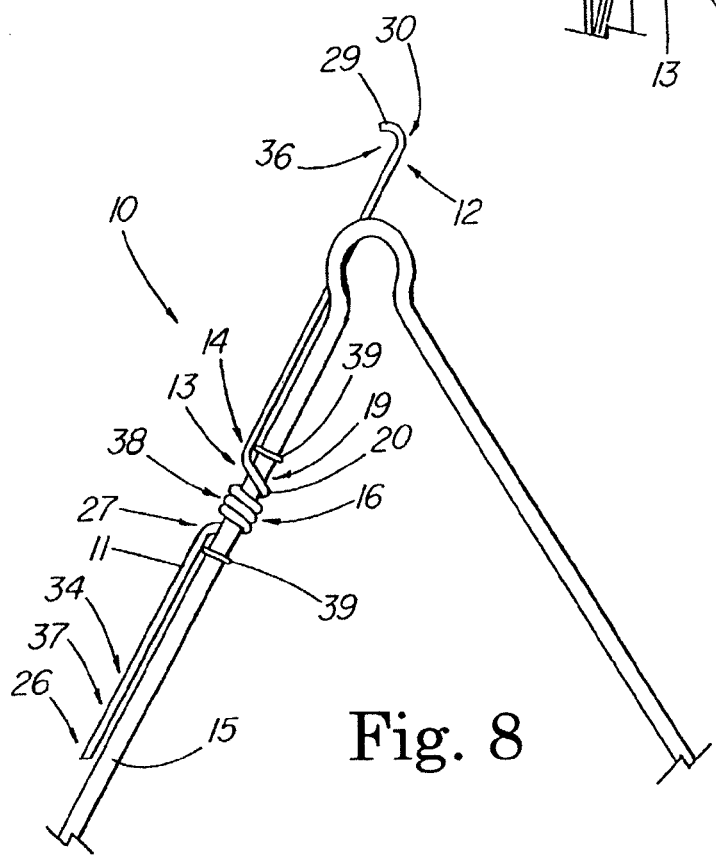
FIG. 8 depicts a side view of an embodiment of the present invention in which the barb includes more than one anchor and associated stress-dispersing region.

FIGS. 2 and 3 depict a barb 11 that includes a helical coil 38 that is wound around the strut 15 to which it is attached. The barb 11 is attached to the strut 15 and is configured to anchor the prosthesis 10. An example of a prosthesis that includes such a barb is the ZENITH™ AAA Endovascular Graft (Cook Incorporated), which may be used to treat an abdominal aortic aneurysm (AAA) located in the vicinity of the aortic bifurcation. In this example, a series of staggered barbs is affixed to the proximal, suprarenal Z-STENT™ (Cook Inc.) to anchor the stent graft within the proximal neck of the aneurysm being treated and to prevent downstream migration of the device which could lead to leakage of blood into the aneurysmal sac. The barbs may be designed to orient away from the heart in the direction of aortic blood flow. Alternatively or additionally, one or more barbs may be designed to orient towards the heart, opposite the direction of aortic blood flow. The orientation of the barb in each of the embodiments of the present invention is determined, not only by where the device is placed in the body (i.e., accounting for the direction of blood or fluid flow), but by the type of barb as well, e.g., whether or not the barb includes a hooked end 29, as depicted in FIG. 8. In addition, barbs of different orientation may be used within the same device.

To form the helical coil 38 of the illustrative barb 11 of FIGS. 2-3, a length of 0.008-0.012" diameter wire (such as 0.01" spring stainless steel wire) is either machine wound or hand wound around the strut 15 so that the strut 15 traverses the lumen 21 formed by the helical coil 38, thus forming a mechanical attachment 17 between the barb 11 and strut 15. This is best shown in FIG. 3. The helical windings 16 of the base 13 have a first pitch 31 in which the windings 16 typically, but not necessarily, lie directly adjacent to one another.

Returning to FIG. 2, low-temperature silver solder, or some other bonding agent, is applied to the windings 16 of the base 13 to form a permanent bond 18 that reinforces the mechanical attachment of the helical windings and secures the barb longitudinally along the strut 15. Besides the illustrative solder joint 18, alternative methods of forming a permanent bond 18 include welding or the use of adhesives.

As depicted in FIGS. 2-3, helical coil 38 includes a winding 20 distal to those of the base 13 and the point of union 19 between the barb 11 and strut. Referred to herein as the free winding 20 because it is neither soldered to the strut, nor is it generally in contact with the strut, except perhaps in an insignificant or incidental way, the free winding comprises the stress-dispersing region 14 of the barb. It should be noted that the free winding 20 does not necessarily completely encircle the substrate of origin or strut and may only constitute a partial winding. The free winding 20 is of a second pitch 32 that is typically greater (more loosely wound) than the first pitch 31 of windings 16 of the base 13, although it is not essential that the basal winding 16 be closely adjacent to one another as depicted.

By enlarging the radius of the winding 20, such that it is no longer contacting the strut 15, the bending stress is more evenly distributed than would be the case if there were a tighter winding (with less pitch), thereby increasing the fatigue life of the barb. Furthermore, the fact that the free winding 20 of the barb is not affixed to, or in contact with, the strut 15 allows the entire free winding 20 to freely flex and distribute most the bending forces over its entire length. This helps prevent the concentration of torsional and bending stresses at the point of union 19 where the barb 11 extends out from the solder joint 18, typically the most common location of barb fracture in the prior art barb illustrated in FIG. 1.

The anchor 12 of the illustrative barb 11 of FIG. 2 comprises a straight section extending from the stress-dispersing portion such that the overall barb 11 length is about 5 mm, the typical range being 3-8 mm, depending on the stent used. The barb 11 extends at an angle 33 from the strut to facilitate the capture of anchoring tissue, the preferred post-deployment angle 33 being about 20-50°, e.g. 35°, in the illustrative embodiment used to anchor the suprarenal stent of a AAA endovascular graft. Due to plastic deformation that may occur during loading of the device into a delivery system, such as a top cap, this angle may be initially formed at a somewhat larger angle 33 (i.e., 40-80°). The distal end 30 of the barb includes a bevel 35 to facilitate penetration of the vessel wall, with the sharp point being oriented toward the strut 15. The particular barb angle 33 and bevel 35 orientation are selected, in part, to ensure that the device 10 can be compressed to a smaller configuration and loaded into the top cap (not shown) of a delivery system and successful deployed therefrom such that the barb 11 does not deform or become caught within the cap, while still being able to resiliently extend outward to its expanded configuration and effectively engage tissue.

FIG. 4 depicts an alternative embodiment of the present invention in which a short piece of metal cannula 22 is used as the mechanical attachment 17 to affix the barb 11 to the strut 15 of the intraluminal prosthesis 10. The base 13 of the barb 11 is secured against the strut 15 by the cannula 22, which is crimped over the barb and/or affixed using a solder joint 18 or some other means of fixation. At the point of union 19 of the barb 11 as it exits the region of attachment 17, the barb 11 assumes a series of bends or curves 24 that comprise the stress-dispersing region 14, after which the anchor 12 extends outward at the appropriate angle from the strut 15. Alternatively, the cannula 22 can be used in combination with another type of mechanical attachment 17, such as the helical windings 16 of FIG. 3 in which the last winding 20 would comprise the stress-dispersing region 14.

Figure 5:
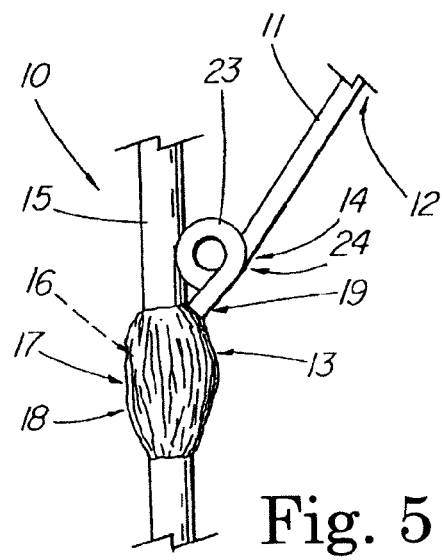
FIGS. 5-5B each depict a side view of an embodiment of the present invention in which the stress-dispersing region of the barb includes a coiled bend.
Figure 5A:
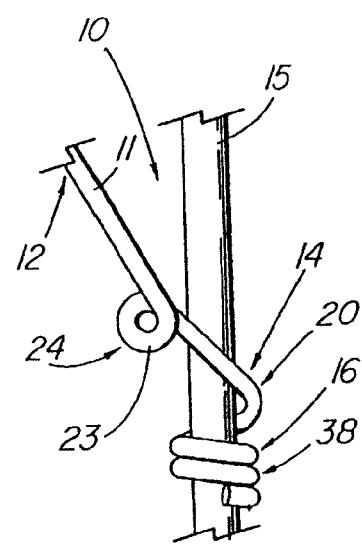
Figure 5B:
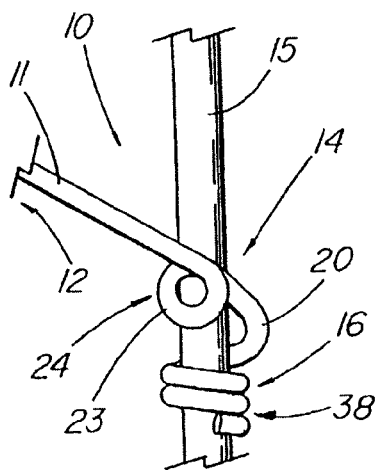
Figure 6:
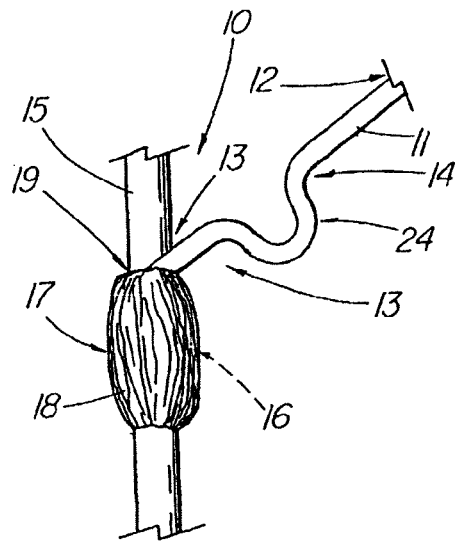
FIG. 6 depicts a side view of an embodiment of the present invention in which the stress-dispersing region of the barb comprises a complex bend.

FIGS. 5-6 depict alternative embodiments of stress-dispersing regions 14 of the barb 11 of the present invention which can be used with a variety of base 13 configurations and types of attachments 17. In the embodiments of FIGS. 5, 5A, and 5B, stress-dispersing region 14 comprises a complete coiled loop 23 whereby the wire makes approximately a one and quarter turn between the base 13 and the anchor 12 of the barb 11. The illustrative loop 23 provides a known mechanical advantage in that it increases the range of flexibility at that bend, as evidenced by its use in certain medical devices, such as stents, and other devices with sharp bends (e.g., safety pins). Although the tighter-radius bends, in general, can provide a site having an increased risk of fracture, this may be more than offset by the added flexibility of the barb, depending on the configuration. FIGS. 5A and 5B depict embodiments that include both the free winding 20 as depicted in the embodiments of FIG. 23, as well as a coiled loop 23 that is located adjacent to the free winding 20. In the embodiment of FIG. 5A, the coil is discrete from the free winding 20, whereas in the embodiment of FIG. 5B, a portion of the coiled loop 23 originates from the free winding 20 such that they are essentially contiguous with one another. The combination of the coiled loop 23 and free winding 20 form a stress-dispersing region 14 having different flexibility characteristics that may be desirous in a particular application.

The embodiment of FIG. 6 includes a generally U-shaped bend 24 that comprises the stress-dispersing region 14. The embodiments of FIGS. 5-6 are merely exemplary of the numerous configurations of bends 24 that can be utilized to redistribute bending stresses and reduce the risk of fracture. These and other undisclosed bends may be used in combination within the stress-dispersing region 14 to further distribute the stress load of the implanted barb 11. Like the embodiments of FIGS. 5a-5b, the bends 24 may be combined with a free helical winding 20 for added flexibility.

Figure 7:
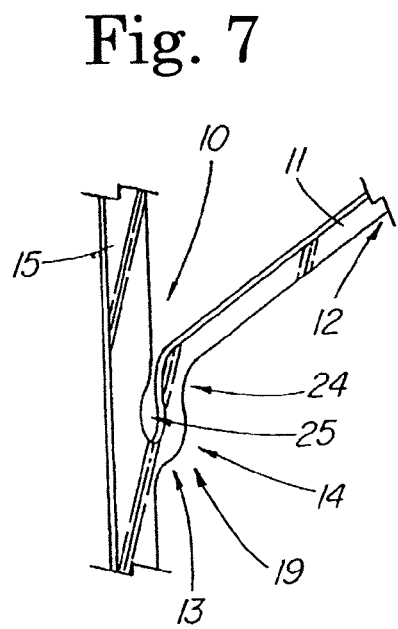
FIG. 7 depicts a side view of an embodiment of the present invention in which the barb is integral with the strut of the stent.

FIG. 7 depicts an integrally formed barb 11 in which the barbed prosthesis 10 is partially or completely formed from a sheet of metal or other material, such as by laser cutting, eliminating the need for a separate attachment mechanism 17. The base 13 of the barb 11 basically comprises the point of union 19 between the strut portion 15 and the barb portion 11 from which it extends. In the illustrative embodiment, the stress-dispersing region 14 comprises a series of bends 24, as well as a fillet 25 at the union 19 with the strut to further reduce stress concentration.

FIG. 8 depicts an embodiment of the present invention in which the prosthesis 10 includes a doubled-ended barb 11 having a first barb portion 36 that includes a first anchor 12 and associated first stress-dispersing portion 14, and a second barb portion 37 that includes a second anchor 26 and associated second stress-dispersing portion 27, all extending from a single base 13, which, in the illustrative embodiment, comprises a helical coil 38 similar to that depicted in FIG. 3. Both the first free winding 20 extending from the first barb portion 36 and the second free winding 27 extending oppositely from the base 13 are unattached to the strut 15 and free to flex and distribute any bending stresses therealong. Additionally, FIG. 8 also illustrates an alternative attachment means between the barb 11 and strut 15, wherein rather than a mechanical attachment 17 or bonding attachment 18, the helical coil 38 is allowed to slide along the strut 15, which may reduce the stress moment along the barb 11 in certain situations. To prevent the barb from sliding too far in either direction, a pair of stops 39, such as beads of solder, welded structure, burs formed in the strut 15, etc. is placed at either end of the base 13. In the illustrative double barb 11, the first barb portion 36 includes a terminal hook 29 for anchoring the device to prevent migration due to blood or fluid flow, while the oppositely oriented second barb portion 37 includes a straight distal end 34. Alternatively, the exemplary double-ended barb 11 can be modified to include other disclosed configurations of the base, stress-dispersing or anchor portions or regions 12,13,14 of the barb 11 or any appropriate means of attachment to the strut 15.

FIGS. 9-15 depict additional exemplary barbs that include various features of the present invention. FIGS. 9A and 9B depict an exemplary retractable barb 110 that is attached to the strut 114 of a prosthesis 112. The barb 110 comprises a base 116 and a retractable body 118 extending distally from the base 116. The base 116 is attached to the strut 114 and the body 118 extends freely from the base 116 and the strut 114 towards a distal anchor 120. The anchor 120 is sized and configured to penetrate tissue adjacent the prosthesis. For example, the anchor 120 may include a beveled end with a sharp point 122 to facilitate penetration of a vessel wall.

The barb 110 has a retracted configuration (not shown) to facilitate loading of the prosthesis into a delivery catheter. Additionally, the barb has an extended configuration (shown in FIGS. 9A and 9B) where the barb 110 extends outwardly from the strut 114 and may engage a surrounding vessel. As explained above, the barb may be attached to the strut by various means, such as welding, soldering, adhesive, or other like techniques.

Figure 9A:
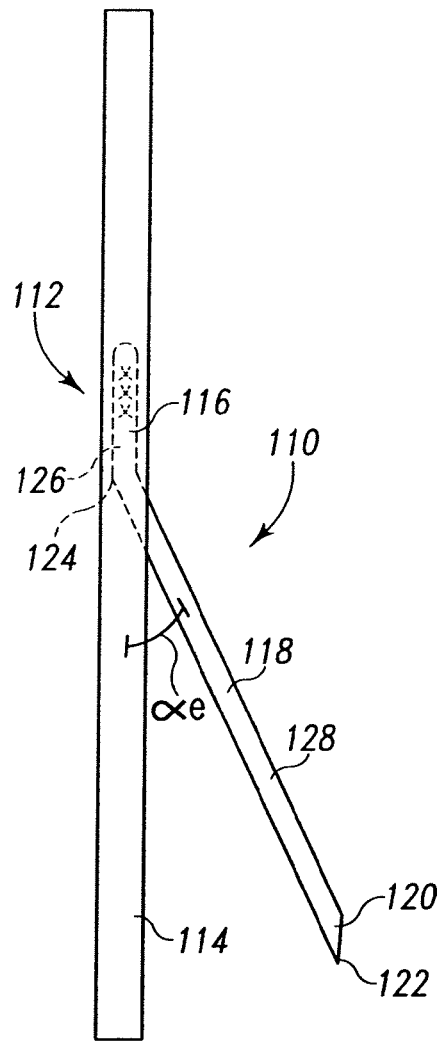
FIGS. 9A-9B depict side and front views of an exemplary retractable barb.
Figure 9B:
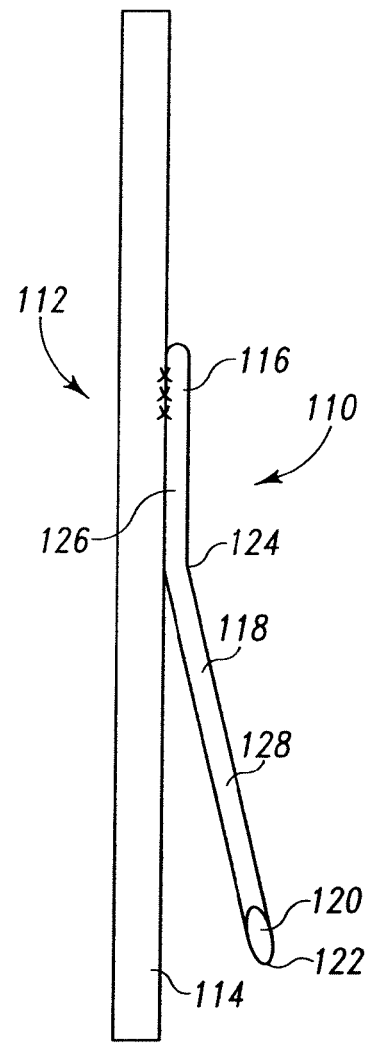

As shown in FIGS. 9A and 9B, the barb body 118 may comprise a hinge 124 disposed between the base 116 and the anchor 120. The anchor 120 is pivotable about the hinge 124 between extended and retracted configurations of the barb. The body 118 further comprises a first arm 126 disposed between the hinge 124 and the base 116, and a second arm 128 disposed between the anchor 120 and the hinge 124. In this example, the first arm 126 extends longitudinally along the strut 114 between the base 116 and the hinge 124 and the second arm 128 extends at an angle to the strut 114 and at an angle to the first arm 126.

In the extended configuration, the anchor 120 is oriented at a first angle with respect to the strut 114 and with respect to the base 116. In the retracted configuration, the anchor 120 is oriented at a second angle with respect to the strut 114 and with respect to the base 116. The angle of the anchor 120 increases with respect to the base 116 from the extended configuration towards the retracted configuration, whereas the angle of the anchor 120 with respect to the strut 114 decreases. The orientation of the anchor 120 may vary depending on the design of the prosthesis. In one example, the extended angle of the anchor 120 with respect to the strut 114 may be about 20-50°, whereas the retracted angle may be about 0-20°. Other extended and retracted angles are contemplated and are within the scope of the present invention.

In general, the anchoring force of a barb may be proportional to the length of the barb body. In typical known devices, the barb body has a fixed and predetermined length. Accordingly, the only way to effect a change in the anchoring force is to trim the body, thus decreasing the length and increasing the anchoring force. Decreasing the length of the body, however, decreases the range of the barb, or the distance that the barb extends from the prosthesis in the extended configuration, and thus may limit the effectiveness of the barb as an anchor. Prior to the present invention, there was no known effective method of tuning a barb to selectively increase or decrease the anchoring force.

One advantage of many of the barbs described in the present application is that the free length of the barb may be changed without affecting the range of the barb. For example, the anchoring force of the barb 110 shown in FIGS. 9A and 9B can be maximized by minimizing the length of the first arm 126. Conversely, the anchoring force of the barb 110 can be minimized by maximizing the length of the first arm 126. The anchoring force of the barb can thus be tuned by selecting an attachment point between the barb 110 and the strut 114 so that the first arm 126 corresponds with a predetermined force. It will be apparent that for this barb, and others disclosed herein, the length of the second arm 128, and thus the range of the barb, is generally independent of the length of the first arm 126.

FIGS. 10A-10C illustrate another exemplary barb 210 that comprises a proximal base 216, a retractable body 218, and a distal anchor 220. A hinge 224 is disposed along the body 218 between the base 216 and the anchor 220 and is spaced apart from the base 216. The barb 210 has an extended configuration, shown generally in FIGS. 10B and 10C, and a retracted configuration, shown generally in FIG. 10A. In contrast with the anchor 220, which is configured to extend radially outwardly from the prosthesis, the hinge 224 is disposed radially inwardly from the prosthesis. Because the hinge 224 is disposed opposite the anchor 220, it will not interfere with the anchoring function in the extended configuration, and it will have a generally negligible effect on the overall profile of the prosthesis in the retracted configuration.

In the extended configuration, the anchor 220 is oriented at a first angle $\alpha_e$ with respect to the base 216 and the strut 214. The anchor 220 extends radially outwardly from the prosthesis so that it can engage a surrounding vessel. In the retracted configuration, the anchor 220 is oriented at a second angle $\alpha_r$ with respect to the base 216 and with respect to the strut 214. In contrast with the example shown in FIGS. 9A and 9B, where the anchor 120 is oriented at a generally obtuse angle with respect to base 116, anchor 220 is oriented at a generally acute angle with respect to base 216.

The barb preferably has a low profile in the retracted configuration to prevent potential damage to the delivery catheter that can be caused by the anchor and to allow the prosthesis to be loaded into a small-diameter catheter for delivery. Accordingly, in the fully retracted configuration, the anchor 220 and the hinge 224 preferably do not extend significantly radially outwardly from the prosthesis. In the example shown in FIG. 10A, in the fully retracted configuration, the anchor is generally parallel to the strut 214 and the hinge 224 is disposed approximately 180° about the strut from the anchor 220.

Barb body 218 comprises a first arm 226 extending between the base 216 and the hinge 224, and a second arm 228 extending between the anchor 220 and the hinge 224. Anchor 220 is pivotable about hinge 224 between extended and retracted configurations via first and second arms 226, 228.

In the retracted configuration, the anchor 220 and the first arm 226 are disposed at a generally acute angle with respect to the base 216, whereas the second arm 228 is disposed at a generally obtuse angle with respect to the base 216. In other examples, the anchor and the first arm 226 may be disposed at a generally obtuse angle with respect to the base 216, and the second arm 228 may be disposed at a generally acute angle with respect to the base 216. In the extended configuration, the anchor 220 and the first arm 226 are disposed at a generally acute angle with respect to the base that is greater than the angle in the retracted configuration.

In the example shown in FIGS. 10A-10C, the first arm 226 extends distally in a first direction with respect to the base 216, and the second arm 228 extends distally in a second direction with respect to the base 216 that is generally opposite the first direction. The hinge 224 joins the first and second arms 226, 228 at an apex 229.

As shown in FIGS. 10A-10C, the barb body 218 may extend longitudinally along and circumferentially about the strut 214. The hinge 224 may have a radius of curvature that corresponds with an outer contour of the strut 214. For example, the hinge 224 may have a radius of curvature that is generally equal to or greater than the radius of a cylindrical strut. In the example shown in FIGS. 10A-10C, the body 218 extends approximately 180° about the strut 214. As shown, the hinge 224 is disposed approximately 90° from the base 216 about the strut 214. In other examples, the body 218 may extend less than or greater than 180° about the strut 214, as required.

Figure 11A:
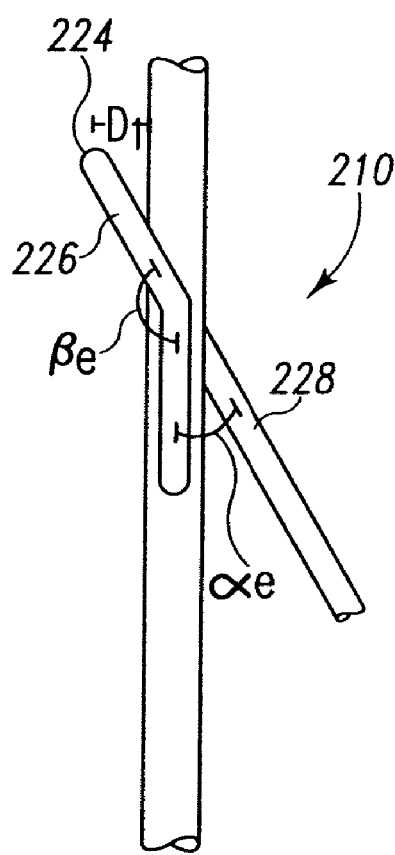
FIGS. 11A-11B depict the kinematics of an exemplary retractable barb.
Figure 11B:
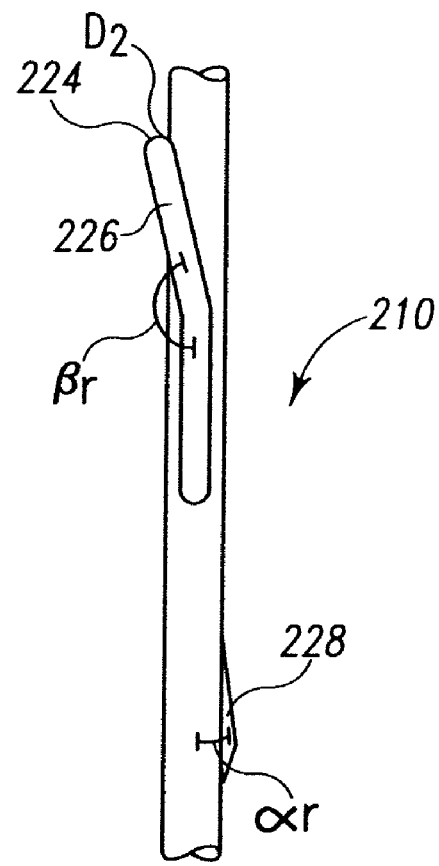

FIGS. 11A and 11B illustrate the kinematics of an exemplary retractable barb 210 during expansion and retraction. In the extended configuration (FIG. 11A), the first arm 226 is disposed at a generally obtuse angle $\beta_e$ with respect to the base 216, the second arm 228 is disposed at a generally acute angle $\gamma_e$ with respect to the strut 214, and the hinge 224 is spaced apart from the strut 214 by a distance $D_1$. The first arm 226 is disposed at a generally acute angle with respect to the second arm 228. In the retracted configuration (FIG. 11B), the first arm 226 is disposed at a generally obtuse angle $\beta_r$ that is greater than $\beta_e$, the second arm 228 is disposed at an angle $\gamma_r$ that is less than $\gamma_e$, and the hinge 224 is spaced apart from the strut 214 by a distance $D_2$ which is less than distance $D_1$. The first arm 226 is disposed at a generally larger acute angle with respect to the second arm 228 than the angle in the extended configuration.

During retraction, the anchor 220 swings towards the strut 214, and the anchor 220 and the second arm 228 pivot about the hinge 224. The angle between the first and second arms 226, 228 increases, whereas the angle between the second arm 228 and the base 216 decreases. The barb 210 bends and twists at the hinge 224 which is spaced apart from the strut 214 by distance $D_1$. This causes the hinge 224 to move inwardly towards the strut 214. As the hinge 224 moves, the first arm 228 pivots about the barb-strut junction so that the angle between the first arm 228 and the base 216 increases.

Barbs, such as those shown in FIGS. 10 and 11, may have many advantages over prior art barbs. For example, because the anchor pivots about the hinge which is spaced apart from the base, the retraction force is not directly transferred to the barb-strut junction. Rather, the retraction force is directed substantially to the hinge. This is important because the barb-strut junction can be a point of weakness, as explained above. Accordingly, such barbs may be stronger and more wear-resistant.

In general, as the distance $D_1$ between the hinge 224 and the strut 214 is decreased, the first arm 226 may pivot over a shorter distance, the hinge 224 may absorb a greater percentage of the retraction force, and less of the retraction force may be transferred to barb-strut junction. In some examples, a retractable barb may be provided where the distance $D_1$ is generally zero. With such a barb, the retraction force may be substantially entirely transferred to and absorbed by the hinge mechanism 124, rather than the barb-strut junction.

Another advantage of such barbs is that the radial anchoring force can be tuned without affecting the range of the anchor. In general, as the length of the first arm increases, the anchor force will decrease, and vice versa. The free length of the barb can be determined during the manufacturing process, for example, by selecting the location of the barb-strut attachment, and thus the length of the first arm. A relatively high anchoring force can be provided by attaching the barb to minimize the length of the first arm. Conversely, a relatively low anchoring force can be provided by attaching the barb to maximize the length of the first arm. One preferred attachment technique is laser welding due to the precision and accuracy of the weld. However, other techniques are contemplated and are within the scope of the present application.

Figure 12A:
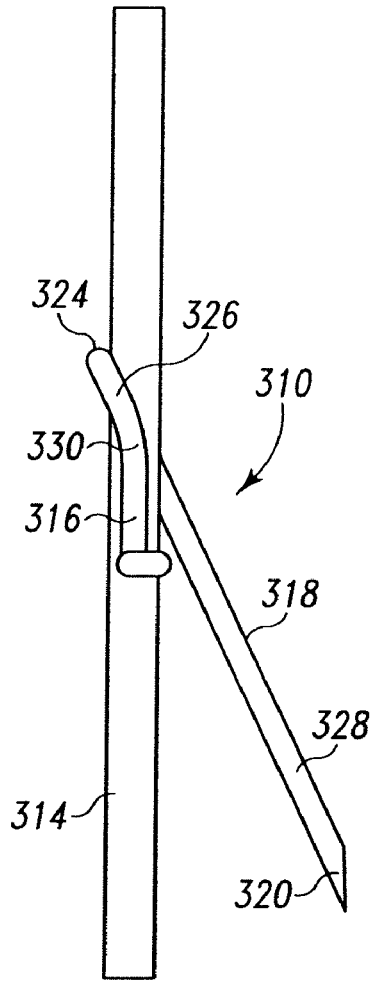
FIGS. 12A-12B, 13A-13B, 14A-14B, and 15A-15B depict side and front views of other exemplary barbs.
Figure 12B:
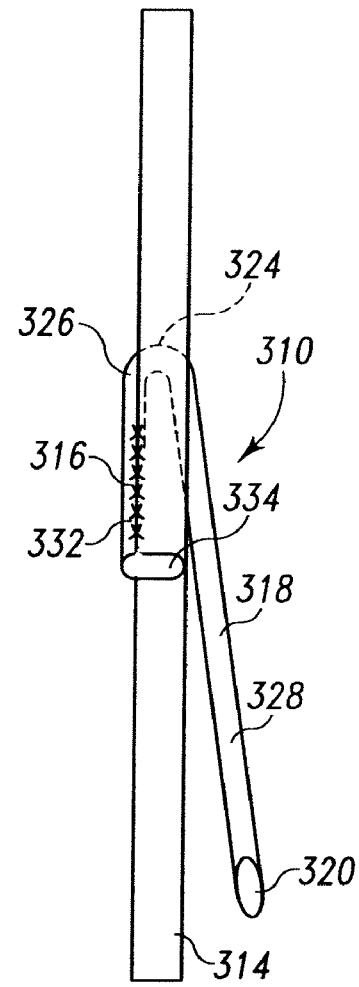

Another exemplary barb 310 is shown in FIGS. 12A and 12B. The barb 310 is attached to a strut 314 and comprises a base 316 and a retractable body 318. The body 318 comprises a distal anchor 320, a hinge 324, a first arm 326, and a second arm 328. As shown, the barb body 318 is substantially similar to the barb body 218 shown and described with respect to FIGS. 10A-10C.

The base 316 comprises a cradle 330 having an inner contour that is sized and shaped to correspond with an outer contour of the strut 314. Accordingly, the base 316 contacts the strut 314 along the entire inner surface of the cradle 330. The base 316 cradles the strut 314 via a longitudinal support component 332 and a radial support component 334. The cradle 330 is used to stabilize or fixture the strut 314 during attachment and helps decrease manufacturing variation and improve the precision in attachment placement. In contrast to barbs that have helically wound bases, the cradle 330 extends only partially about the strut 314 so that the barb 310 can be easily attached to the strut 314 without threading the barb over the strut.

Figure 13A:
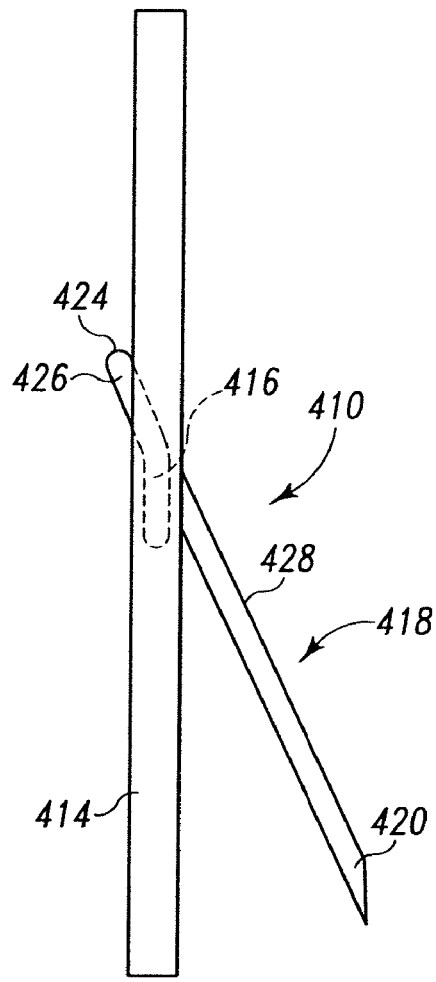
Figure 13B:
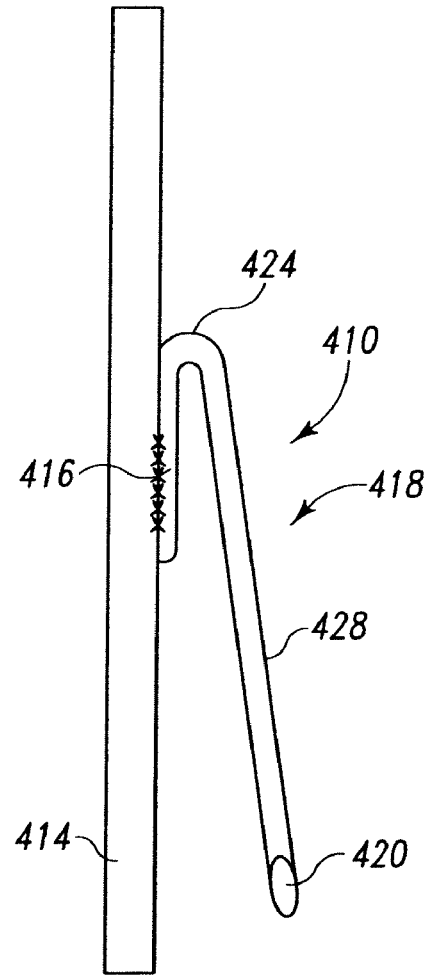

FIGS. 13A and 13B show another barb 410 comprising a base 416, a distal anchor 420, and a hinge 424. A first arm 426 extends distally along the barb from the base 416 towards the hinge 424 in a first direction with respect to the base 416. A second arm 428 extends distally along the barb from the hinge 424 in a second, generally opposite direction with respect to the base 416.

In many respects, barb 410 is similar to barb 210, shown and described with respect to FIGS. 10A-10C. For example, the hinge 424 extends radially inwardly from the prosthesis and the anchor extends radially outwardly from the prosthesis. In contrast with the example shown in FIGS. 10A-10C, barb 410 does not extend circumferentially about the strut 314. Rather, barb 410 extends distally away from the base 416 along the entire barb body 418.

Anchor 420 pivots about the hinge 424 via the second arm 428 between extended and retracted configurations. Accordingly, stress on the anchor 420 is not directly transferred to the barb-strut junction, but rather is absorbed, in whole or in part, by the hinge 424. As the second arm 428 moves between the retracted and extended configurations, the hinge 424 bends and twists, which causes the first arm 426 to pivot about the body-strut junction, as shown and described with regards to FIG. 11. If the force required to pivot the second arm 428 is relatively low in relation to the force required to pivot the first arm 426, the first arm 426 may remain generally stationary as the anchor 420 retracts.

The relative pivot forces of the arms of a retractable barb may be adjusted, for example, by varying the length of the first arm with respect to the second arm. Alternatively, the relative pivot forces of the arms may be adjusted by varying the thickness of the arms, of the hinge, or by otherwise varying the flexural properties thereof.

Figure 14A:
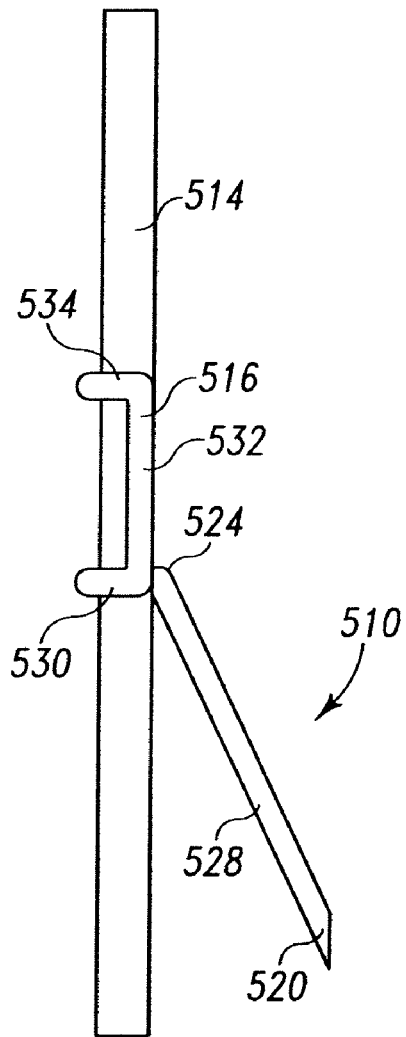
Figure 14B:
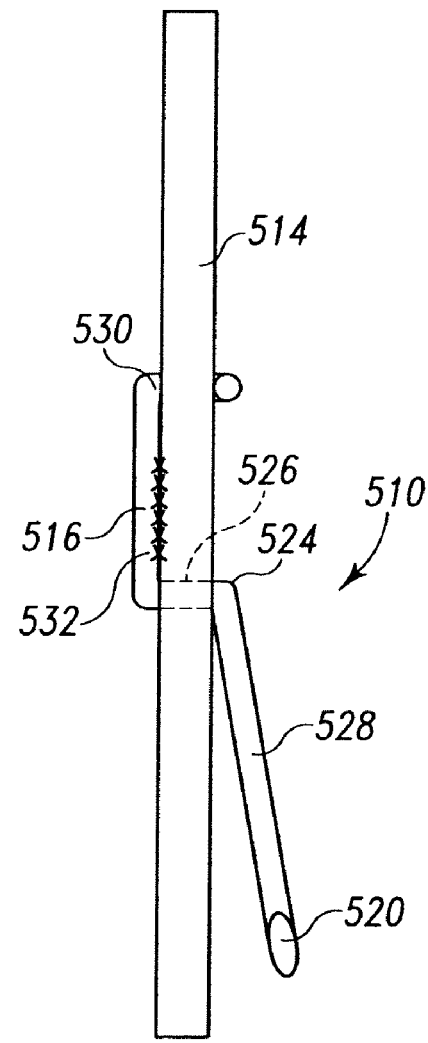

FIGS. 14A and 14B illustrate another retractable barb 510. The barb 510 comprises a base 516 and a distal anchor 520. A first arm 526 is disposed between the base 516 and a hinge 524, and a second arm 528 is disposed between the anchor 520 and the hinge 524. In the fully-extended configuration, the second arm 528 extends at a generally obtuse angle with respect to the base 516 and at a generally obtuse angle with respect to the first arm 526. The second arm 528 extends at a generally acute angle with respect to the strut 514. The anchor 520 pivots substantially about the hinge 524, rather than the barb-stent junction, between extended and retracted configurations. Accordingly, the retraction force is directed to the hinge 524, rather than the barb-strut junction. In the fully retracted configuration, the first arm 526 is disposed at a generally acute angle with respect to the second arm 528 and the strut 514.

The base 516 comprises a cradle 530 having an inner contour that is sized and shaped to correspond with an outer contour of the strut 514. The cradle 530 has a longitudinal component 532 and a radial component 534 and extends only partially about the strut 514. For example, as shown in FIGS. 14A and 14B, the cradle may extend 180° or less about the strut 514. In another example, the cradle 530 may extend 180° or more about the strut 514. Accordingly, the base 516 may be "snapped" into place about the strut via the cradle, creating a mechanical and frictional engagement therebetween. The barb 510 can then be further secured to the strut, for example, by soldering, welding, or the like.

Figure 15A:
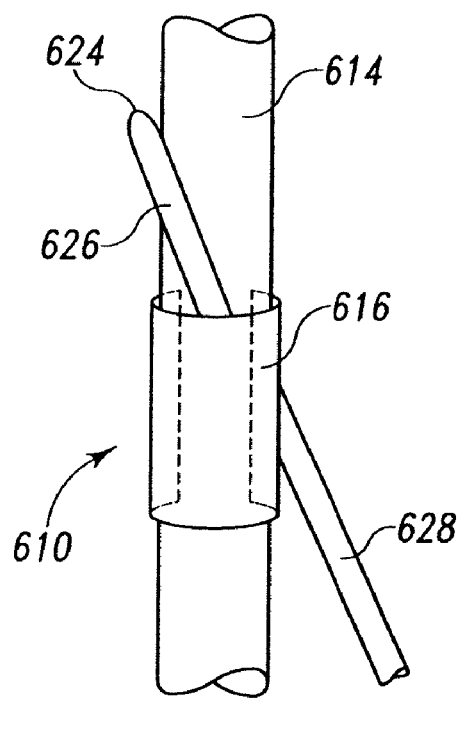
Figure 15B:
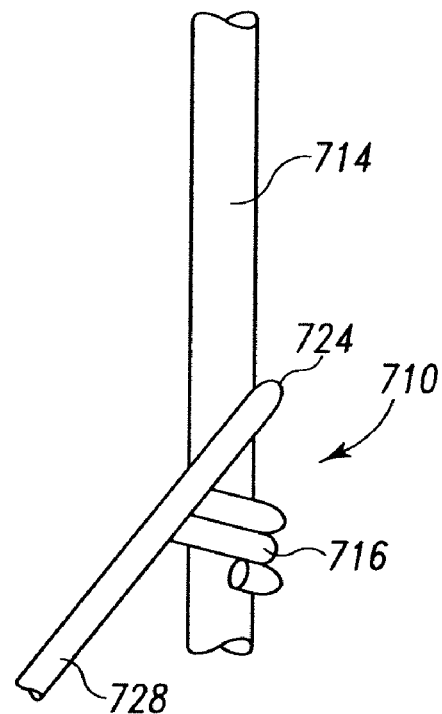

FIGS. 15A and 15B show additional examples of systems for anchoring a prosthesis. In FIG. 15A, a barb 610 comprises a base 616 that extends only partially about the strut 614. The barb 610 further comprises a hinge 624, an anchor (not shown), a first arm 626, and a second arm 628, as described above. In FIG. 15B, a barb 710 comprises a base 716 that comprises a helical winding, a hinge 724, a distal anchor (not shown), a first arm (hidden), and a second arm 728.

In each of the examples shown in FIGS. 15A and 15B, the first arm 626, (hidden), is disposed at a generally acute angle with respect to the second arm 628, 728 in both extended and retracted configurations, and the angle therebetween increases from the extended configuration to the retracted configuration as the anchor (not shown) pivots about the hinge 624, 724. In each example, the second arm 628, 728 is disposed at an acute angle with respect to the base 616, 716 in both extended and retracted configurations. Additionally, the hinges 624, 724 are positioned radially inward from the prosthesis, whereas the anchors (not shown) extend radially outward from the prosthesis.

A barb of the present invention may be manufactured, for example, by bending a single unitary wire to form the barb body and base. Alternatively, two or more wires may be joined and bent to form the retractable barb. In other examples, (see, for example, FIG. 15A) the entire barb may be cut from a flat sheet of material or from a cannula and subsequently bent and shaped to the desired configuration. Typical cutting methods include, for example, laser cutting, EDM, high-pressure jet, chemical etching, machining, grinding, and/or stamping. A barb may be made of any suitable material such as nitinol or stainless steel. In order to minimize the potential for corrosion, the barb may preferably comprise a material that has similar or the same electrochemical properties as the material of the support structure.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27.sup.th edition.

The invention claimed is:

1. A system for anchoring an endoluminal prosthesis comprising:
   a barb comprising a base and a retractable body extending distally from the base towards a distal anchor, where the retractable body comprises:
      a hinge disposed between the base and the anchor and spaced apart from the base;
      a first arm disposed between the base and the hinge;
      a second arm disposed between the anchor and the hinge;
      a retracted configuration; and
      an extended configuration;
   where the anchor pivots about the hinge between the retracted configuration and the extended configuration.

2. The system of claim 1, further comprising a support structure, where the support structure comprises a strut and the barb base is attached to the strut.

3. The prosthesis of claim 2, where at least a portion of the barb body extends longitudinally along and circumferentially about the strut.

4. The prosthesis of claim 2, where the hinge is spaced apart from the strut by a first distance in the extended configuration and by a second distance that is less than the first distance in the retracted configuration.

5. The prosthesis of claim 2, where the base comprises a cradle having an inner contour corresponding with an outer contour of the strut.

6. The prosthesis of claim 2, where the anchor is disposed radially outwardly from the support structure and the hinge is disposed radially inwardly from the support structure.

7. The system of claim 2, where the first arm has a length corresponding with a predetermined barb anchoring force.

8. The system of claim 1, where in the extended configuration, the first arm is disposed at a generally acute angle with respect to the second arm.

9. The system of claim 1, where the angle between the first arm and the second arm increases from the retracted configuration towards the extended configuration.

10. The system of claim 1, where the angle between the second arm and the base increases from the retracted configuration towards the extended configuration.

11. The system of claim 1, where the first arm extends distally in a first direction with respect to the base and the second arm extends distally in a second direction with respect to the base that is generally opposite the first direction.

12. The system of claim 1, further comprising:
a support structure comprising a strut, where the barb base is attached to the strut and where:
   at least a portion of the barb body extends longitudinally along and circumferentially about the strut;
   the hinge is spaced apart from the strut by a first distance in the extended configuration and by a second distance that is less than the first distance in the retracted configuration;
   the base comprises a cradle having an inner contour corresponding with an outer contour of the strut;
   the anchor is disposed radially outwardly from the support structure and the hinge is disposed radially inwardly from the support structure; and
   the first arm has a length corresponding with a predetermined barb anchoring force;
and where:
   in the extended configuration, the first arm is disposed at a generally acute angle with respect to the second arm;
   the angle between the first arm and the second arm increases from the retracted configuration towards the extended configuration;
   the angle between the second arm and the base increases from the retracted configuration towards the extended configuration; and
   the first arm extends distally in a first direction with respect to the base and the second arm extends distally in a second direction with respect to the base that is generally opposite the first direction.

13. A system for anchoring an endoluminal prosthesis comprising:
a support structure; and
a barb comprising a base, an anchor, and a hinge disposed between the base and the anchor and spaced apart from the base;
where the base is attached to the support structure and where the anchor pivots about the hinge between a retracted configuration and an extended configuration;
where the barb further comprises an arm disposed between the base and the hinge having a length corresponding with a predetermined barb anchoring force.

14. The system according to claim 13, where the support structure comprises a strut and the barb base is attached to the strut.

15. The system according to claim 14, where the hinge is spaced apart from the strut by a first distance in the extended configuration and by a second distance that is less than the first distance in the retracted configuration.

16. The system according to claim 14, where at least a portion of the barb distal of the base extends longitudinally along and circumferentially about the strut.

17. The system according to claim 13, where the barb further comprises a second arm disposed between the anchor and the hinge and the angle between the first arm and the second arm increases from the retracted configuration towards the extended configuration.

18. The system according to claim 13, where the barb further comprises a first arm disposed between the base and the hinge, and a second arm disposed between the anchor and the hinge, where:
   the angle between the first arm and the second arm increases from the retracted configuration towards the extended configuration;
   the support structure comprises a strut and the barb base is attached to the strut;
   the hinge is spaced apart from the strut by a first distance in the extended configuration and by a second distance that is less than the first distance in the retracted configuration; and
   at least a portion of the barb distal of the base extends longitudinally along and circumferentially about the strut.

19. A method of tuning an anchor for an endoluminal prosthesis, the method comprising the steps of:
providing a retractable barb comprising a proximal end and a distal end, where a distal portion of the barb comprises an anchor;
providing a support structure for an endoluminal prosthesis;
determining a free length of the barb that corresponds with a predetermined barb anchoring force; and
selectively attaching the barb to the support structure so that the length of the barb that extends freely from the support structure is generally equal to the free length.

* * * * *